United States Patent [19]

Cheng

[11] Patent Number: 5,355,877
[45] Date of Patent: Oct. 18, 1994

[54] MOUTH-TO-MOUTH RESUSCITATION DEVICE HAVING A SEALED VALVE POSITION TO PROTECT A RESCUER

[76] Inventor: Yu W. Cheng, 3F, No. 2-3, 181 Lane, Chia-Hsing Street, Taipei, Taiwan

[21] Appl. No.: 56,655

[22] Filed: May 3, 1993

[51] Int. Cl.⁵ .................. A61M 16/00; A62B 9/06
[52] U.S. Cl. .................. 128/203.11; 128/202.28; 128/207.14
[58] Field of Search .............. 128/202.28–203.11, 128/207.15, 201.28, 205.24, 207.14, 911

[56] References Cited

U.S. PATENT DOCUMENTS

| | | | |
|---|---|---|---|
| 3,626,936 | 12/1971 | Barker | 128/203.11 |
| 4,106,502 | 8/1978 | Wilson | 128/203.11 |
| 4,819,627 | 4/1989 | Connors | 128/203.12 |
| 4,819,628 | 4/1989 | Eisenberg et al. | 128/203.11 |
| 4,858,605 | 8/1989 | Levy | 128/203.12 |
| 4,886,057 | 12/1989 | Nave | 128/203.11 |
| 4,909,245 | 3/1990 | Wollenhaupt | 128/203.12 |
| 4,969,456 | 11/1990 | Cooper | 128/203.11 |
| 5,088,485 | 2/1992 | Schock | 128/203.11 |
| 5,119,809 | 6/1992 | Gerson | 128/203.12 |
| 5,127,397 | 7/1992 | Kohnke | 128/203.11 |

FOREIGN PATENT DOCUMENTS

2176406 12/1986 United Kingdom ........... 128/202.29

Primary Examiner—Kimberly L. Asher
Attorney, Agent, or Firm—W. Wayne Liauh

[57] ABSTRACT

The present invention discloses an improvement of a mouth-to-mouth resuscitation device characterized in that it has a lower casing and an upper casing separated by a pliable and elastic diaphragm. The elastic diaphragm is upheld by two struts affixed to the lower casing and urged against the bottom of the upper casing to seal any communication between the upper casing and the lower casing and thus preventing air from leaking into said upper casing from lower casing under normal conditions. When the diaphragm is urged by air pressure from the upper casing the portions of the diaphragm not being upheld by the struts will be bent down to allow air to flow into the lower casing. And when the air pressure from said blow-in portion stops, the diaphragm will return to its normally closed portion and seal the upper chamber from the lower chamber.

1 Claim, 10 Drawing Sheets

(Prior Art)

FIG 11

MOUTH-TO-MOUTH RESUSCITATION DEVICE HAVING A SEALED VALVE POSITION TO PROTECT A RESCUER

BACKGROUND OF THE INVENTION

The present invention relates to an improvement for a mouth-to-mouth resuscitation device. Upheld by struts at the internal sides of a lower casing, a diaphragm is thus securely attached to the bottom of an upper casing whereby air blown by the first-aid person will not flow back to the upper casing and enter his/her mouth through the lower casing, and in addition the patient's breathing air will not leak into the upper casing.

Figure 11:
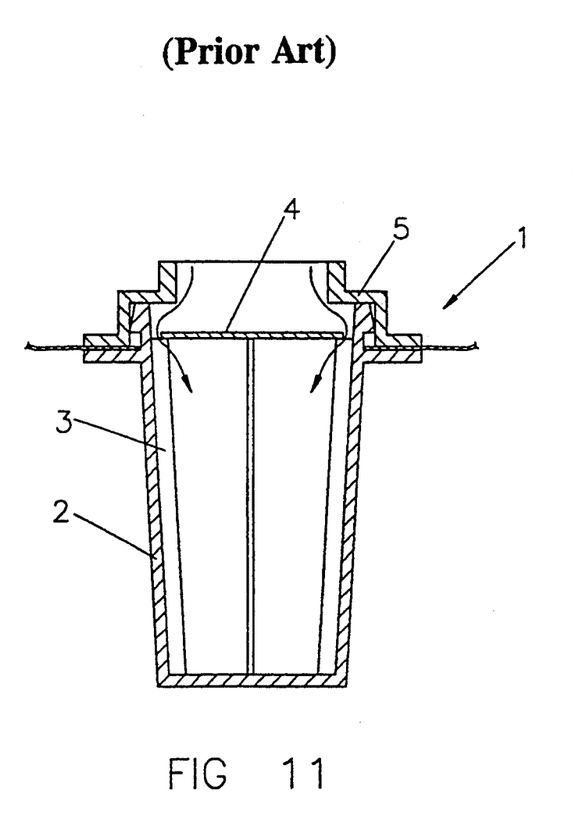
FIG. 11 is a perspective view of the conventional heart-lung supportive device.

The mouth-to-mouth resuscitation device currently on the market is as as shown in FIG. 11 wherein the lower casing 2 incorporates a certain number of struts 3 and under stationary conditions these struts 3 uphold a diaphragm 4 which maintains an appropriate distance relative to the upper casing. When the first-aid person is blowing air toward the patient, air exhaled from the patient will blow the lower casing 2 upward so that the diaphragm 4 will be closely connected with the upper casing 5 to prohibit air exhaled from the patient from flowing back into the upper casing. Notwithstanding, if the patient's breathing strength is too weak to blow the diaphragm upward and the passage into the upper casing remains open, and the air is allowed to flow back into the rescuer's mouth, and providing air exhaled from the patient is carrying germs, or spittles coughed out or thrown up by the patient, which may carry AIDS virus. This is likely to cause the rescuer to be infected and therefore results in a great risk to the rescuer.

Viewing those defects found in the conventional hear-lung supportive device, the inventor thus has devoted himself to the research and therefore has accomplished the improvement through the experience of design and production in relevant field and continuous modifications and tests.

SUMMARY OF THE INVENTION

The present invention has been accomplished under the circumstances in view. It is an object of the present invention to provide an improvement for the heart-lung supportive device.

Another object of the present invention is to provide an improvement for a mouth-to-mouth resuscitation device to prevent air from flowing from the patient's mouth into the rescuer's mouth.

These and other objects and advantages of the present invention will become apparent to those skilled in the art after considering the following detailed specification together with the accompanying drawings.

DETAILED DESCRIPTION OF THE PREFERRED EMBODIMENTS

Figure 1:
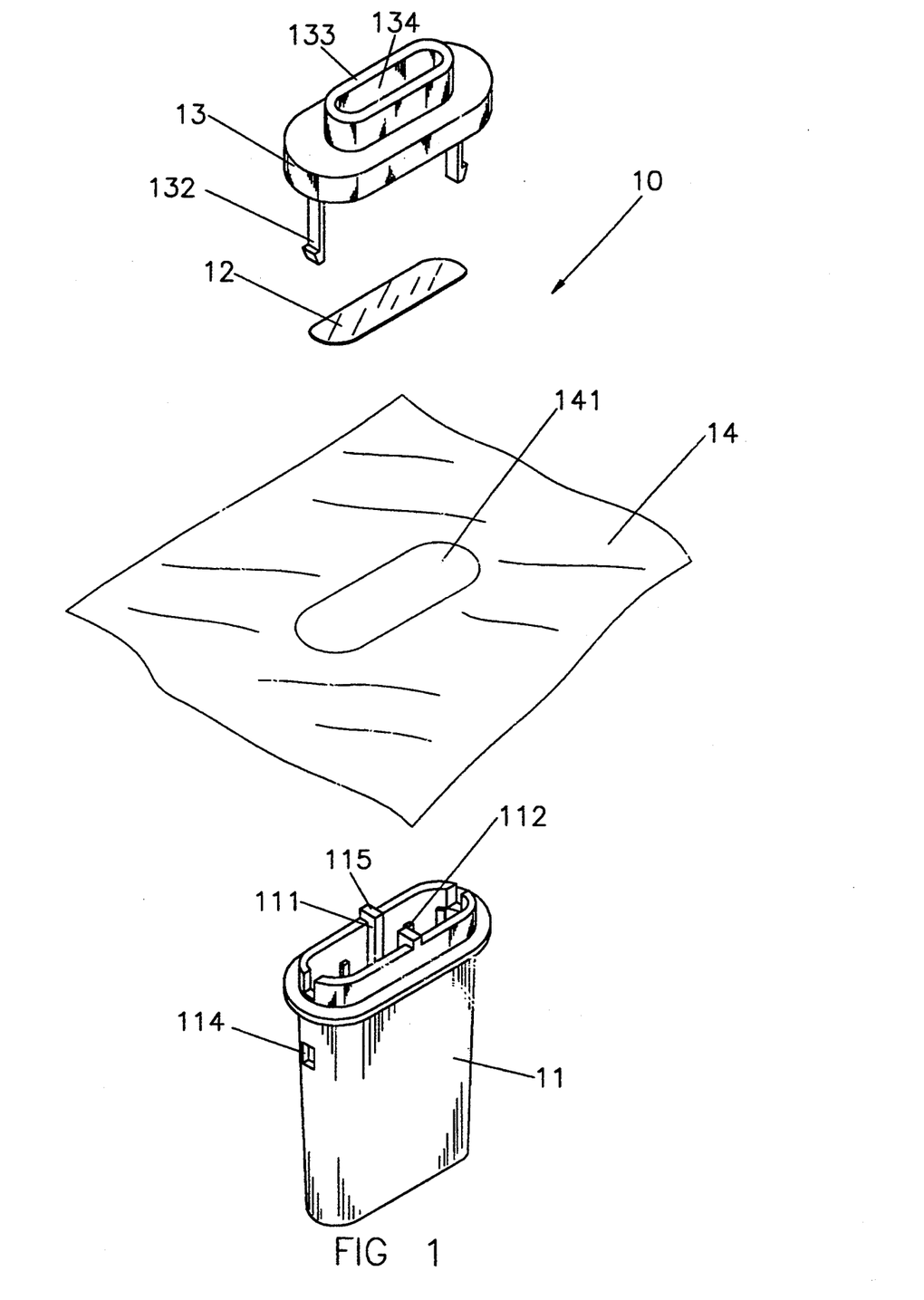
FIG. 1 is a cutaway elevational view of the present invention, showing the relationship among various components.
Figure 2:
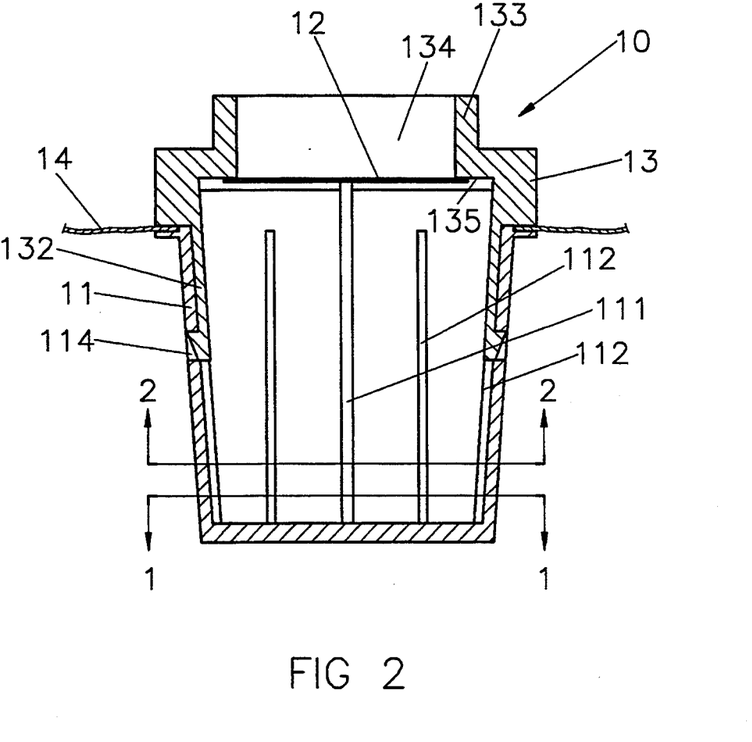
FIG. 2 is a perspective view of the present invention, showing the relationship between the diaphragm and the struts.
Figure 3:
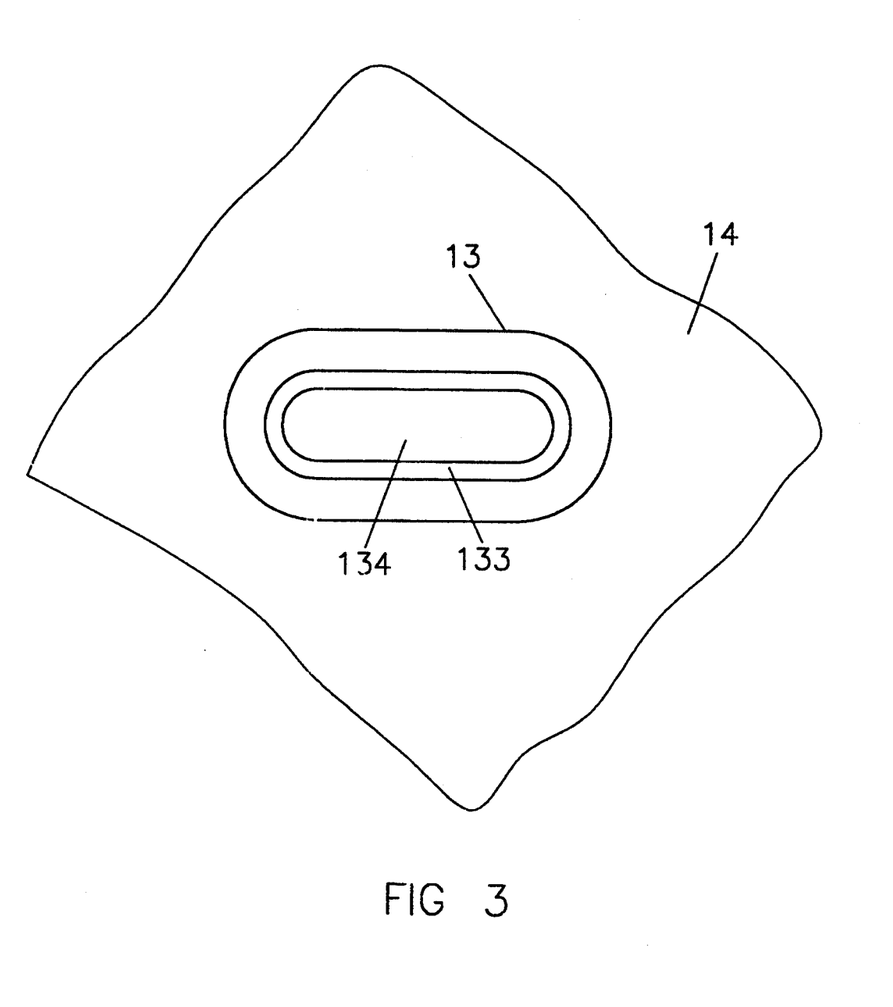
FIG. 3 is a top view of the present invention, showing the top structure of the present invention.
Figure 4:
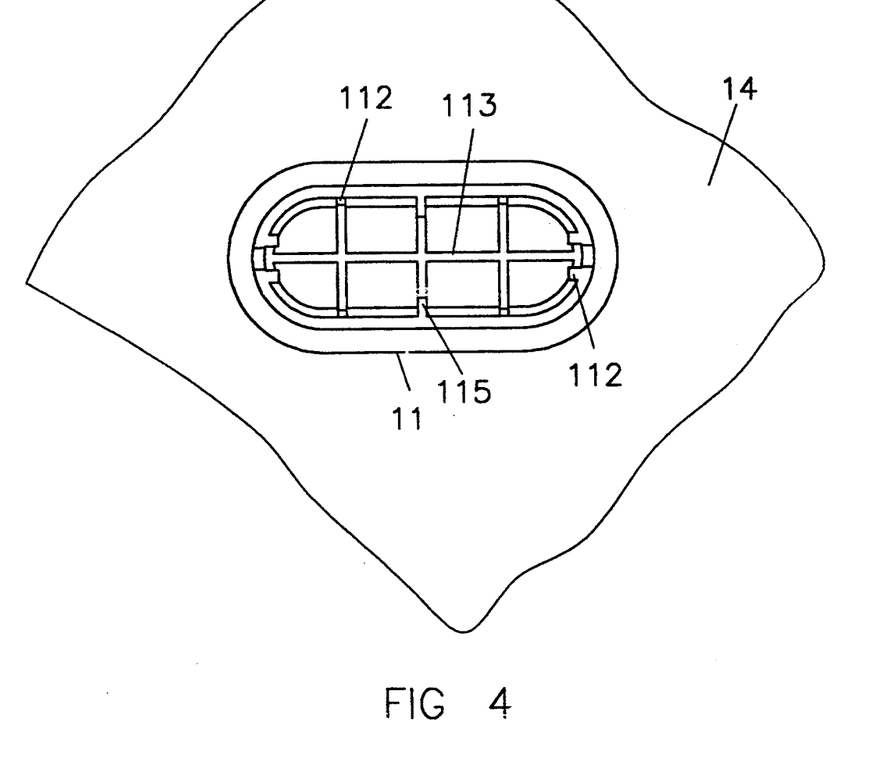
FIG. 4 is a top view of the present invention, showing the present invention where the upper casing is removed.
Figure 5:
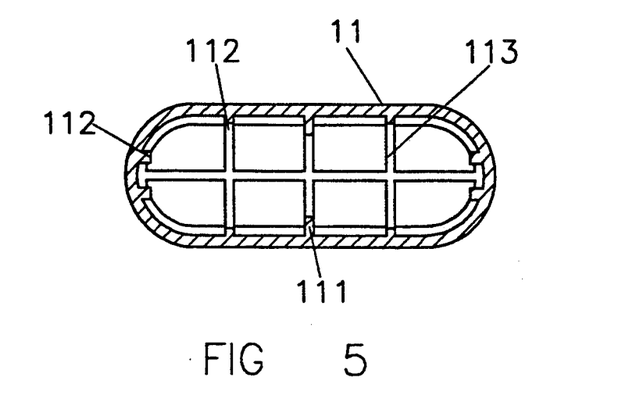
FIG. 5 is an enlarged perspective view of the bottom structure of the lower casing taken on line A—A of FIG. 2.
Figure 6:
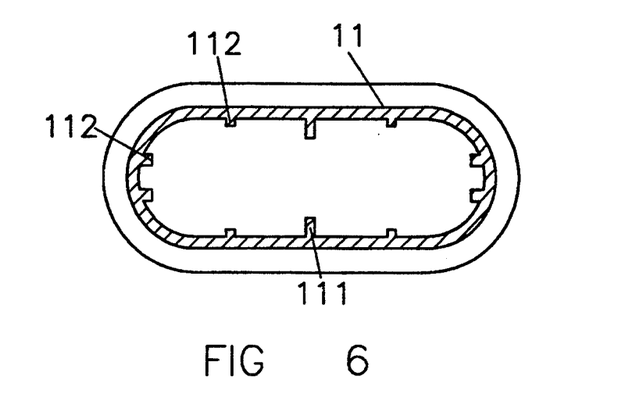
FIG. 6 is an enlarged perspective view of the sectional structure of the lower casing taken on line B—B of FIG. 2.
Figure 7:
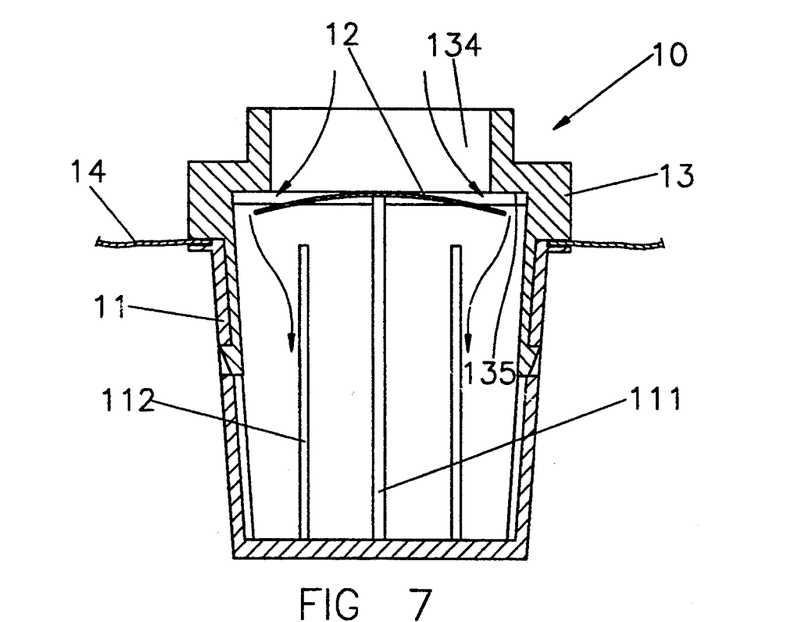
FIG. 7 is a side perspective view of the present invention, showing the action of the diaphragm when air is blown in by the first-aid person.

Referring to FIGS. 1 and 2, the present invention relates to an improvement a mouth-to-mouth resuscitation device wherein the diaphragm 12 is upheld by the struts 111 at the internal sides of the lower casing 11. The diaphragm 12 is elastic and normally maintains closely connected with the upper casing 13. When air enters the upper casing 13 the diaphragm 12 will bend and form a spacing with the upper casing 13 to allow air to pass therethrough and again closely connect with the upper casing 13 after air has passed by. The elasticity and construction of the diaphragm thus allows it to function like a check valve that prohibits air from return flow to accomplish the effect of close and non-return.

Referring to the drawings, the lower casing 11 resembles a hollow shape and each side has a fastening hole 114 and bottom side has a guard net 113 to prohibit foreign matter from falling into the patient mouth. And the internal wall of the lower casing 11 has a certain number of ribs 112 for reinforcing purpose and especially the center position of the internal wall has a plural struts 111 which project over the top side and internal wall of the lower casing 11 and uphold the diaphragm 12 with their top sides 115.

As shown in FIGS. 1, 2, 7 and 8, the diaphragm 12 resembles an elliptical shape and its area is slightly smaller than the top of the lower casing 11 and is located on the top 115 of the struts 111. Upheld by the struts 111, the diaphragm 12, which is very flexible and elastic, will maintain a normally closed state in conjunction with the upper casing 13 in a stationary (i.e., no flow) condition.

The upper casing 13 resembles a hollow shape and its top side has a blow-in portion 133 while the narrower sides of its bottom are projected with a fastening mortice 132, and the blow-in portion 133 has a vertically-through chamber 134. The diaphragm 12 on the top of the lower casing 111 and upheld by the struts 11, when the upper casing 13 has fastened together with the lower casing 11, lays against the bottom 135 of the blow-in portion 133 to cover the chamber 134 and keep the chamber 134 closed under normal state.

The center position of the transparent stopper 14 is cut with a fitting hole 141 slightly greater than the section of the lower casing 11. During the assembly of the mouth-to-mouth resuscitation device of the present invention the transparent stopper 14 is fitted between the upper casing 13 and the lower casing 11 so as to prohibit the first-aid person's face from being splashed by spittle coughed out or thrown up by the patient, and to provide an air way shield whereby air exhaled from the patient will exhaust toward all directions out of the spacing between the stopper 14 and the patient's cheek without contact with the first-aid person and therefore to insure the safety of the first-aid person. The assembly of the present invention is illustrated below.

Referring to FIGS. 1 and 2, for the assembling of the present invention: first, fastening the fitting hole 141 of the transparent stopper 14 together with the lower casing 11, second, placing the diaphragm 12 on the top 115 of the struts 111 of the lower casing 11, covering the upper casing onto the lower casing, at that moment the retaining mortice 132 at each side of the upper casing 13 will be fitted into the fastening hole 114 of the lower casing 11 to accomplish the effect of fastening together securely. Upon assembly of the present invention, the intermediate section of the diaphragm 12 is upheld with the top 115 of the struts and laid against the bottom 135 of the blow-in portion 133 to seal the chamber 134 whereby when the present invention maintains at normal state the chamber 134 appears close.

Figure 8:
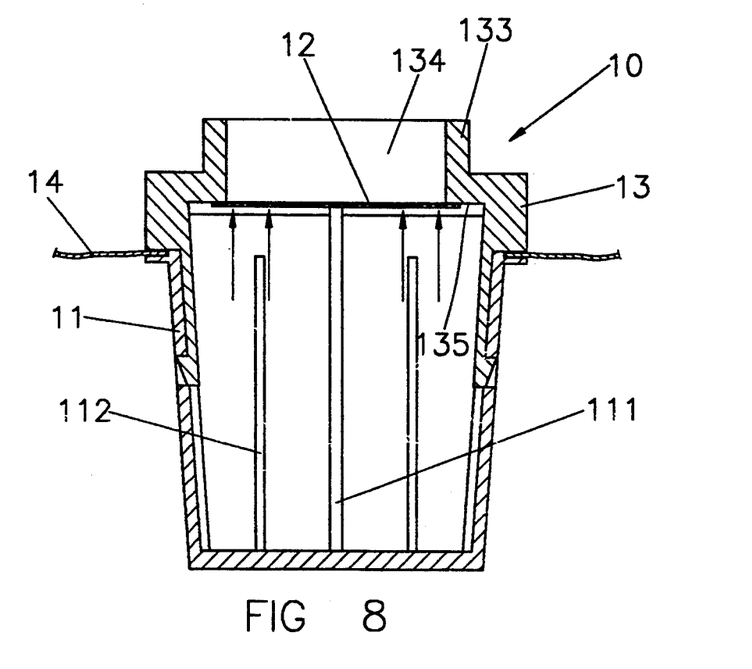
FIG. 8 is a side perspective view of the present invention, showing the action of the elastic and pliable diaphragm prohibiting air from return flow when the first-aid person stops blowing air.
Figure 9:
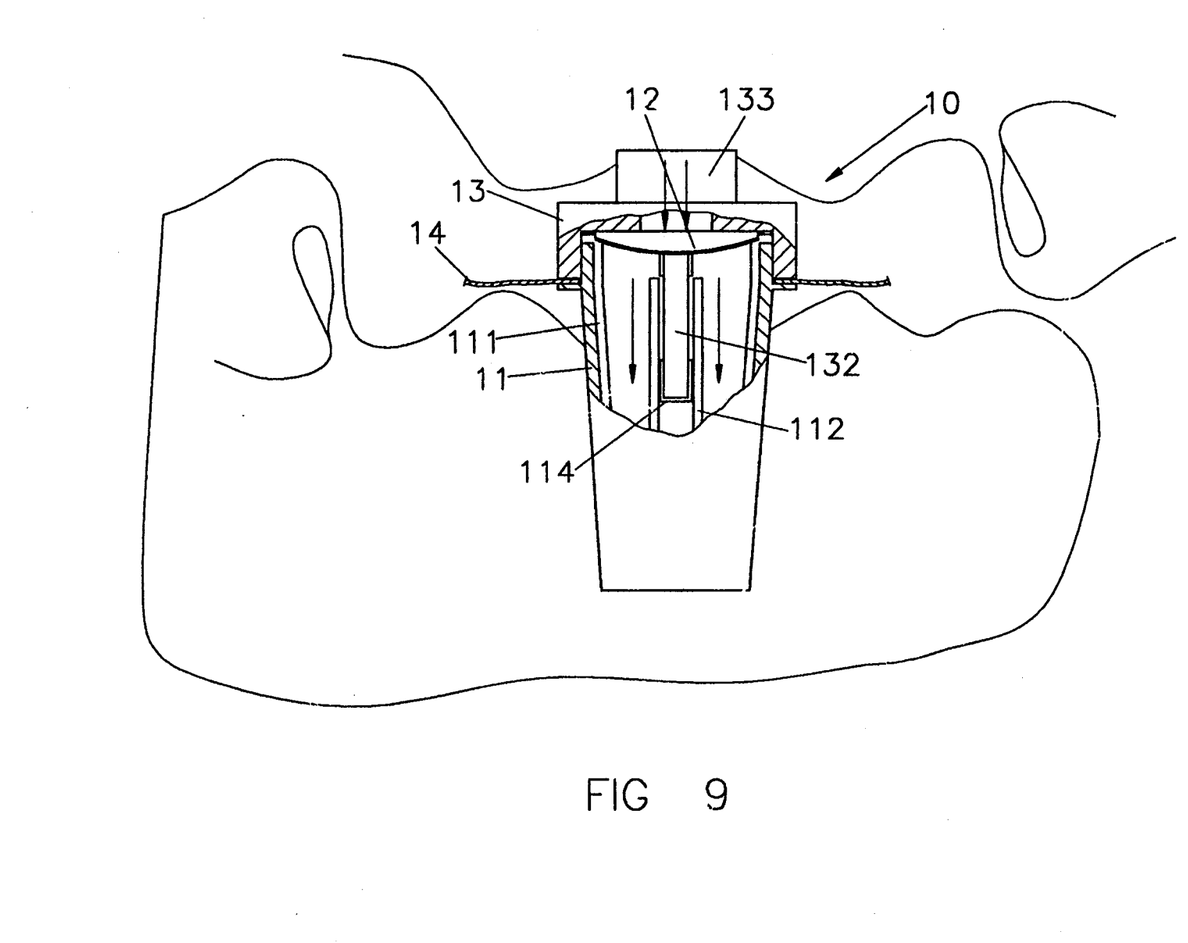
FIG. 9 is a partially perspective view of the embodiment according to the present invention, showing air blown by the first-aid person has entered the patient's mouth through the diaphragm.
Figure 10:
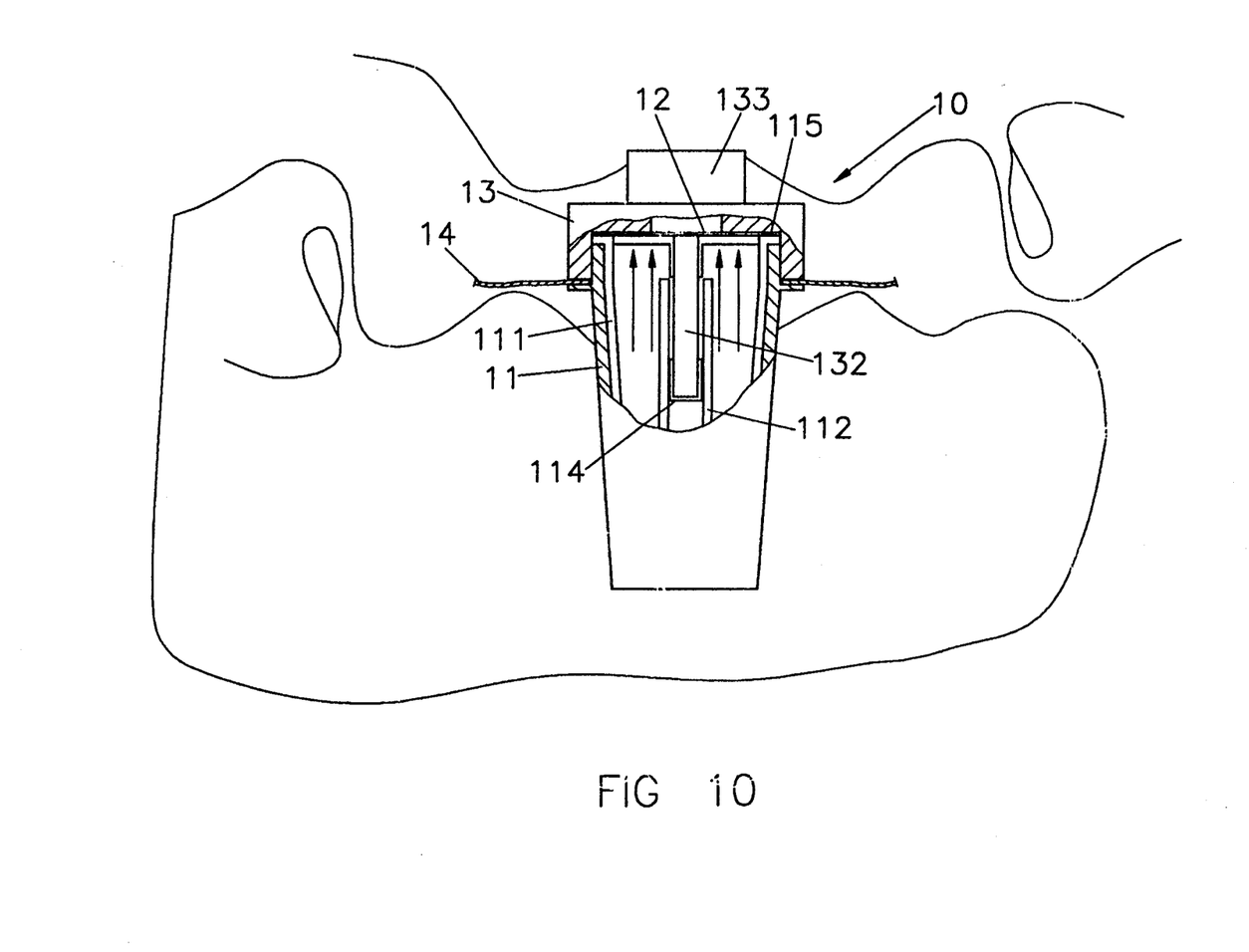
FIG. 10 is a partially perspective view of the embodiment according to the present invention, showing when the first-aid person stops blowing, the diaphragm has sealed the inlet to prohibit air exhaled from the patient from flowing back.

Referring to FIGS. 8, 9 and 10, during the use of the present invention, the lower casing 11 is put in the patient's mouth, at the moment the transparent stopper 14 has covered the peripheral area of the patient mouth to prohibit the first-aid person's face from being splashed by spittle coughed out or thrown up by the patient accidently; during operation the first-aid person can blow air in the chamber of the blow-in portion 133 of the upper casing, when air flows toward the diaphragm 12 from the chamber 134 the diaphragm 12 will be bent down using the two struts 111 as the bending point as a result of air pressure. At the moment the diaphragm 12 will become open and air is allowed to pass through the diaphragm 12, flow to the lower casing 11 and further enter the patient's mouth. When the first-aid person stops blowing, the diaphragm 12 will restore to its original shape with its own elasticity as a result of air pressure disappeared while the chamber 134 will close again to form a check valve device whereby any air exhaled from the patient is prohibited from passing through the diaphragm 12 to ensure that the air exhaled or thrown-up from the patient will not flow back and leak out of the chamber 134 of the upper casing 13. Therefore the use of the present invention is effective to prohibit air exhaled from the patient from entering the first-aid person's mouth but to exhaust through the spacing between the lower side of the stopper 14 and the patient's face whereby even if air exhaled from the patient is very weak the effect of prohibition will be accomplished the same to insure the safety of the first-aid person.

Many change, modifications, variations and other uses and applications of the subject invention will, however, become apparent to those skilled in the art after considering the foregoing specification together with the accompanying drawings. All such changes, modifications, variations and other uses and applications which do not depart from the spirit and scope of the invention are deemed to be covered by the invention which is limited only by the claims which follow.

What is claimed is:

1. A mouth-to-mouth resuscitation device comprising:

a lower casing resembling a hollow cylinder having an internal wall, a top and a bottom, the internal wall having a top and the bottom having a guard net;

an upper casing adapted to be fastened to the top of said lower casing, said upper casing having a blow-in portion, said blow-in portion having a top, a bottom and a chamber;

fastening means for fastening said lower casing with said upper casing and forming an air passage therebetween;

closing means for closing said passage between said upper casing and said lower casing, said closing means comprising a floating diaphragm disposed between said upper casing and said lower casing, said floating diaphragm being a pliable and elastic sheet slightly smaller than the sectional area of the top of said lower casing, said floating diaphragm further being unattached to either said upper casing or said lower casing and easily replaced;

a transparent stopper sheet fitted between said upper casing and said lower casing;

said closing means further comprising means to prevent leaking of patient fluids past said floating diaphragm, said leak preventing means including a holding means for positively holding said floating diaphragm between said upper casing and said lower casing and against the bottom of said blow-in portion, said holding means comprising two opposing struts affixed to the internal wall of said lower casing and extending beyond the top of the internal wall of said lower casing;

said floating diaphragm being upheld by said two struts of said lower casing and urged against the bottom of the blow-in portion of said upper casing when said upper casing and said lower casing are fastened together to thereby seal the chamber of the blow-in portion from communicating with said lower casing thus preventing air from leaking into said upper chamber from said lower casing under normal conditions;

portions of said floating diaphragm not being upheld by said struts bending and allowing air to flow into said lower casing responsive to air blowing through said blown-in portion said diaphragm returning to its normally closed and sealing position responsive to lack of air blowing through said blown-in portion, thus said floating diaphragm provides a function of a normally closed check valve prohibiting air from flowing back into said blow-in portion or any leaking between said lower chamber and said blow-in portion.

* * * * *